United States Patent [19]
Klioze et al.

[11] 3,980,787
[45] Sept. 14, 1976

[54] 3-PHENYLSPIRO[ISOBENZOFURAN-1,4'-PIPERIDINE]SULFENAMIDES AND DERIVATIVES

[75] Inventors: Solomon S. Klioze, Flemington; William J. Novick, Jr., Lebanon, both of N.J.

[73] Assignee: American Hoechst Corporation, Bridgewater, N.J.

[22] Filed: Aug. 25, 1975

[21] Appl. No.: 607,600

[52] U.S. Cl. .............................. 424/267; 260/293.58
[51] Int. Cl.² ...................................... C07D 405/04
[58] Field of Search ................ 260/293.58; 424/267

[56] References Cited
UNITED STATES PATENTS

| | | | |
|---|---|---|---|
| 3,635,956 | 1/1972 | Krapcho | 260/240 K |
| 3,686,186 | 8/1972 | Houlihan | 260/293.58 |

*Primary Examiner*—G. Thomas Todd
*Attorney, Agent, or Firm*—Curtis, Morris & Safford

[57] ABSTRACT

Novel 3-phenylspiro[isobenzofuran-1,4'-piperidine]sulfenamides and derivatives and a method of preparing the same are described. These compounds are useful as diuretic and antihypertensive agents.

15 Claims, No Drawings

3-PHENYLSPIRO[ISOBENZOFURAN-1,4'-PIPERIDINE]SULFENAMIDES AND DERIVATIVES

This invention relates to novel 3-phenylspiro[isobenzofuran-1,4'-piperidine]sulfenamides and derivatives which are useful as diuretics, to methods of preparing same, to methods of treatment with pharmaceutically effective amounts thereof, and to pharmaceutical compositions containing such compounds as essential active ingredients.

To the best of our knowledge, the compounds of this invention have not heretofore been described or suggested. Spiro[phthalan-piperidine]s of the formula

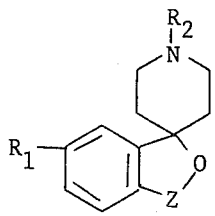

in which $R_1$ is hydrogen, lower alkyl, lower alkoxy, halogen or trifluoromethyl, $R_2$ is hydrogen or benzyl, and Z is —CH$_2$— or —CO—, described by W. J. Houlihan et al. in U.S. Pat. No. 3,686,186, are outside the scope of the invention as are the 1,3-dihydrospiro[isobenzofuran]s described by Bauer et al. in U.S. application Ser. No. 424,080 and 424,117, both filed Dec. 12, 1973, by Duffy in U.S. application Ser. No. 596,163, filed July 15, 1975 and by Klioze et al. in U.S. application Ser. No. 573,145, filed Apr. 30, 1975. The same applies to the spiro piperidines described by Marxer et al. [J. Org. Chem., 40, No. 10, 1427 (1975)] and the natural product of the formula

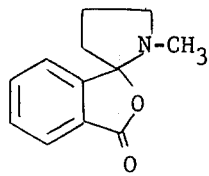

described by Y. Inubushi et al.. [Chem. and Pharm. Bull. (Japan), 12, 749 (1964)].

The compounds of this invention are significantly different from the compounds of the prior art and exhibit unanticipated pharmacological activity.

The 3-phenylspiro[isobenzofuran-1,4'-piperidine]sulfenamides and derivatives of this invention have the formula

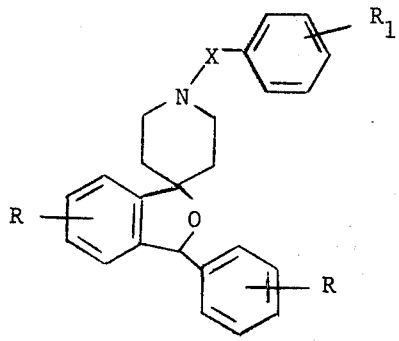

wherein R is hydrogen, halogen, lower alkoxy, lower alkyl or hydroxy; $R_1$ is hydrogen, lower alkoxy, halogen, lower alkyl, nitro or amino; and X is —S—, —SO— or —SO$_2$—.

The preferred compounds are those wherein $R_1$ is hydrogen and X is —S—.

The compounds of the invention are prepared by the following method wherein R and $R_1$ are as defined earlier. The starting materials are described in U.S. application Ser. No. 424,117 filed Dec. 12, 1973.

A 1,3-dihydro-3-phenylspiro[isobenzofuran-1,4'-piperidine] of the formula

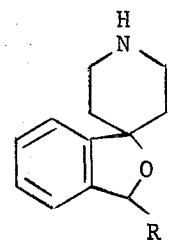

is allowed to react with a R-phenylsulfenyl, R-phenylsulfonyl or R-phenylsulfinyl halide in the presence of an organic solvent and an acid scavenger at ambient temperature to produce a compound of the invention. A preferred system is one in which the halide is a chloride, the organic solvent is methylene chloride and the acid scavenger is triethylamine.

Additionally a compound of the invention wherein $R_1$ is nitro can be catalytically reduced with hydrogen to afford the corresponding amino compound.

The compounds of the invention are useful as diuretic agents due to their ability to produce diuresis in mammals. Diuretic activity is measured in rats by a method described by C. M. Kagawa and M. J. Kalm, Arch. Intern. Pharmacodyn. 137, 241 (1962). Drugs are dosed orally to a group of rats and the average volume of urine excreted is compared to (divided by) the average volume excreted by a positive control group of rats dosed orally with 1000 mg/kg of urea, a known diuretic agent. The resulting drug/urea ratios, if greater than one, are indicative of diuretic activity. The diuretic activity in this test of representative compounds of this invention and of chlorthiazide, a standard diuretic, is shown in Table I.

TABLE I

| Compound | Dose (mg/kg) | Drug/urea ratio |
| --- | --- | --- |
| 1,3-dihydro-1'-phenylsulfenyl-3-phenylspiro[isobenzofuran-1,4'-piperidine] | 25 | 2.2 |
| 1,3-dihydro-1'-phenylsulfinyl-3-phenylspiro[isobenzofuran-1,4'-piperidine] | 50 | 1.7 |
| 1,3-dihydro-1'-(4-nitrophenylsulfenyl)-3-phenylspiro[isobenzofuran-1,4'-piperidine] | 50 | 1.7 |
| 1,3-dihydro-1'-(4-methoxyphenylsulfenyl)-3-phenylspiro[isobenzofuran-1,4'-piperidine] | 50 | 1.5 |
| chlorthiazide | 50 | 1.3 |

Compounds of the invention are also useful as antihypertensive agents due to their ability to depress blood pressure in mammals. Antihypertensive activity is measured in the spontaneous hypertensive rat by the indirect tail cuff method described by A. Schwartz, Ed., *Methods in Pharmacology*, Vol. I, page 135, Appleton-Century-Crafts, New York, New York 1971. In this procedure a group of 5 animals is treated orally with the drug for 3 days in relation to a control group of the same number. The drop in blood pressure is measured on the 3rd day following administration. The antihypertensive activity, expressed as mm Hg decrease in mean arterial blood pressure in this test, of some of the compounds of this invention is set forth in Table II.

TABLE II

| Compound | Dose (mg/kg of body weight) | mm Hg |
| --- | --- | --- |
| 1,3-dihydro-1'-phenyl-sulfenyl-3-phenylspiro-[isobenzofuran-1,4'-piperidine] | 25 | −44 |
| 1,3-dihydro-1'-phenyl-sulfinyl-3-phenylspiro-[isobenzofuran-1,4'-piperidine] | 100 | −22 |

The above data illustrates that the compounds of the present invention are useful for producing diuresis and for the treatment of hypertension when administered to mammals at doses of from 0.1 to 100 mg/kg of body weight.

The compounds of the present invention may be administered to a patient by a convenient route such as orally, intramuscularly, intraveneously, subcutaneously or intraperitoneally. The preferred route of administration is oral, for example, with an inert diluent or with an edible carrier or in gelatin capsules or tablets.

For the purpose of oral therapeutic administration, the active compounds of this invention may be incorporated with excipients and used in the form of tablets, troches, capsules, elixirs, suspensions, syrups, wafers, chewing gum, and the like. These preparations should contain at least 0.5% of active compound, but may be varied depending upon the particular form and may conveniently be between 7 to about 70% by weight of the unit. The amount of active compound in such compositions is such that a suitable dosage will be obtained. Preferred compositions and preparations according to the present invention are prepared so that an oral dosage unit form contains between 1 and 200 milligrams of active compound.

The tablets, pills, capsules, troches, and the like may also contain the following ingredients: a binder such as gum tragacanth or gelatin; an excipient such as starch or lactose, a disintegrating agent such as alginic acid, potato starch and the like; a lubricant such as magnesium stearate; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain various other materials which modify the physical form of the dosage unit, for example, coatings. Thus, tablets or pills may be coated with sugar, shellac, or both. A syrup may contain, in addition to the active compounds, sucrose as a sweetening agent, preservatives, colorings, materials and flavors. Materials used in preparing these various compositions must be pharmaceutically pure and non-toxic in the amounts utilized.

For the purpose of parenteral therapeutic administration, the active compounds of the invention may be incorporated into a solution or suspension. These preparations should contain at least 0.1% of active compound, but may be varied to be between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediamine-tetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Examples of other compounds of the invention are 1,3-dihydro-3-(4-fluorophenyl)-1'-phenylsulfinyl-spiro[isobenzofuran-1,4'-piperidine];
1,3-dihydro-3-(4-methoxyphenyl)-1'-phenylsulfenyl-spiro[isobenzofuran-1,4'-piperidine];
1,3-dihydro-6-fluoro-1'-[(4-methoxyphenyl)sulfenyl]-3-phenylspiro[isobenzofuran-1,4'-piperidine];
1,3-dihydro-5-methoxy-1'-phenylsulfonyl-3-phenyl-spiro[isobenzofuran-1,4'-piperidine];
1,3-dihydro-1'-phenylsulfonyl-3-(4-tolyl)-spiro[isobenzofuran-1,4'-piperidine];
1,3-dihydro-6-fluoro-3-(4-fluorophenyl)-1'-phenyl-sulfonylspiro[isobenzofuran-1,4'-piperidine];
1,3-dihydro-6-hydroxy-1'-(4-nitrophenyl)sulfenyl-3-phenylspiro[isobenzofuran-1,4'-piperidine];
1,3-dihydro-1'-(4-chlorophenyl)sulfenyl-3-phenyl-spiro[isobenzofuran-1,4'-piperidine];
1,3-dihydro-3-phenyl-1'-(4-tolylsulfenyl)-spiro[isobenzofuran-1,4'-piperidine]; and
1,3-dihydro-1'-(4-aminophenyl)sulfenyl-3-phenyl-spiro[isobenzofuran-1,4'-piperdine].

The present invention is further illustrated by the following examples.

EXAMPLE 1

To a solution of 1.3 g of 1,3-dihydro-3-phenyl-spiro[isobenzofuran-1,4'-piperidine] and 0.61 g of triethylamine in 25 ml of methylene chloride is added dropwise with stirring under nitrogen a solution of 0.80 g of phenylsulfenyl chloride in 10 ml of methylene chloride. The resulting solution is stirred for 3 hours at ambient temperature, diluted with 50 ml of methylene chloride, and washed successively with water and a 1N sodium hydroxide solution, dried and the solvent removed leaving a yellow oil. The oil is triturated with an ether-petroleum ether mixture to yield a nearly colorless crystalline solid which is recrystallized from ethanol to give fine colorless plates, mp 130°–133°C., of 1,3-dihydro-1'-phenylsulfenyl-3-phenylspiro[isobenzofuran-1,4'-piperidine].

Analysis: Calculated for $C_{24}H_{23}NOS$: 77.18%C; 6.21%H; 3.75%N; 8.58%S. Found: 77.10%C; 6.25%H; 3.77%N; 8.42%S.

EXAMPLES 2 AND 3

By following the procedure outlined above in Example 1, substituting phenylsulfinyl chloride and 4-methoxyphenylsulfenyl chloride for phenylsulfenyl chloride produces, respectively, the compounds listed below in Table III.

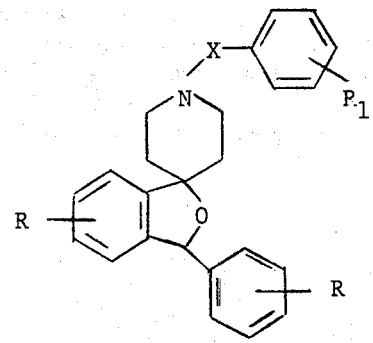

TABLE III

| Ex | m.p. °C | Empirical Formula | Calculated | | | | Found | | | |
|---|---|---|---|---|---|---|---|---|---|---|
| | | | %C | %H | %N | %S | %C | %H | %N | %S |
| 2 | 167–171 | $C_{24}H_{23}NO_2S$ | 74.00 | 5.95 | 3.60 | 8.23 | 73.80 | 5.65 | 3.43 | 8.34 |
| 3 | 140–143* | $C_{25}H_{25}NO_2S$ | 74.41 | 6.24 | 3.47 | 7.95 | 74.34 | 6.42 | 3.48 | 7.68 |

*After 2 crystallizations.

EXAMPLE 4

To a solution of 2.7 g of 1,3-dihydro-3-phenylspiro[isobenzofuran-1,4'-piperidine] and 1.2 g of triethylamine in 50 ml of methylene chloride is added dropwise with stirring under nitrogen a solution of 1.8 g of phenylsulfonyl chloride in 20 ml of methylene chloride. The reaction mixture is stirred at ambient temperature for 2.5 hours, diluted with 75 ml of methylene chloride, washed successively with water and 1N sodium hydroxide solution, dried, and the solvent removed leaving a yellow solid. The solid is triturated with an ether-petroleum ether mixture to yield a white crystalline solid which is suspended in 50 ml of ethanol, boiled, cooled to 0°C., and filtered leaving a pure white crystalline solid, mp 204°–206°C., of 1,3-dihydro-1'-phenylsulfonyl-3-phenylspiro[isobenzofuran-1,4'-piperidine].

Analysis: Calculated for $C_{24}H_{23}NO_3S$: 71.08%C; 5.72%H; 3.45%N; 7.91%S. Found: 70.90%C; 5.86%H; 3.32%N; 7.91%S.

EXAMPLE 5

To a solution of 4.0 g of 1,3-dihydro-3-phenylspiro[isobenzofuran-1,4'-piperidine] and 1.8 g of triethylamine in 75 ml of methylene chloride is added dropwise with stirring under nitrogen a solution of 3.1 g of 4-nitrophenylsulfenyl chloride in 30 ml of methylene chloride. The reaction mixture is stirred for 3 hours at ambient temperature, diluted with 150 ml of methylene chloride, washed consecutively with water and 1N sodium hydroxide solution, dried and the solvent removed leaving a dark brown oil. The oil is chromatographed on silica gel using chloroform as the eluant. The chloroform is evaporated in vacuo and the residue is triturated with an ether-petroleum mixture and cooled to provide a light brown solid. The solid is fractionally crystallized from ethanol and the second fraction is fine yellow leaflets, mp 168°–170°C., of 1,3-dihydro-1'-(4-nitrophenylsulfenyl)-3-phenylspiro[isobenzofuran-1,4'-piperidine].

Analysis: Calculated for $C_{24}H_{22}N_2O_3S$: 68.87%C; 5.30%H; 6.69%N; 7.66%S. Found: 68.95%C; 5.40%H; 6.72%N; 7.68%S.

We claim:
1. A compound of the formula wherein R is hydrogen, methyl, methoxy, halogen or hydroxy; $R_1$ is hydrogen, methyl, methoxy, halogen, nitro or amino; and X is —S—, —SO— or —SO$_2$—.

2. A compound as defined in claim 1 wherein $R_1$ is hydrogen, methoxy or nitro.

3. A compound as defined in claim 1 of the formula

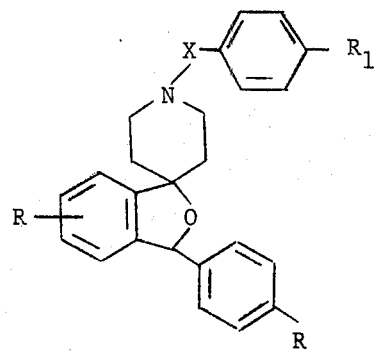

4. A compound as defined in claim 3 wherein $R_1$ is hydrogen, methoxy or nitro.

5. A compound as defined in claim 4 wherein X is —S—.

6. A compound as defined in claim 4 wherein X is —SO—.

7. A compound as defined in claim 4 wherein X is —SO$_2$—.

8. The compound defined in claim 1 which is 1,3-dihydro-1'-phenylsulfenyl-3-phenylspiro]isobenzofuran-1,4'-piperidine].

9. The compound defined in claim 1 which is 1,3-dihydro-1'-phenylsulfinyl-3-phenylspiro[isobenzofuran-1,4'-piperidine].

10. The compound defined in claim 1 which is 1,3-dihydro-1'-(4-methoxyphenyl)sulfenyl-3-phenylspiro[isobenzofuran-1,4'-piperidine].

11. The compound defined in claim 1 which is 1,3-dihydro-1'-phenylsulfonyl-3-phenylspiro[isobenzofuran-1,4'-piperidine].

12. The compound defined in claim 1 which is 1,3-dihydro-1'-(4-nitrophenyl)sulfenyl-3-phenylspiro[isobenzofuran-1,4'-piperidine].

13. A method of treating hypertension which comprises administering to a patient a physiologically effective amount of a compound defined in claim 1.

14. A method of producing diuresis which comprises administering to a patient a physiologically effective amount of a compound defined in claim 1.

15. A pharmaceutical composition which comprises between 0.5 and about 70% by weight of a compound defined in claim 1 as an essential active ingredient, the balance being a pharmaceutically acceptable carrier therefor.

* * * * *